United States Patent
Kano et al.

(10) Patent No.: US 11,728,034 B2
(45) Date of Patent: Aug. 15, 2023

(54) MEDICAL EXAMINATION ASSISTANCE APPARATUS

(71) Applicant: Canon Medical Systems Corporation, Otawara (JP)

(72) Inventors: Yusuke Kano, Nasushiobara (JP); Anri Sato, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 514 days.

(21) Appl. No.: 17/007,028

(22) Filed: Aug. 31, 2020

(65) Prior Publication Data

US 2021/0065905 A1    Mar. 4, 2021

(30) Foreign Application Priority Data

Sep. 2, 2019    (JP) ................ 2019-159598

(51) Int. Cl.
*G06K 9/00*    (2022.01)
*G16H 50/20*    (2018.01)
(Continued)

(52) U.S. Cl.
CPC ............ *G16H 50/20* (2018.01); *G16H 30/20* (2018.01); *G16H 30/40* (2018.01); *G16H 40/40* (2018.01);
(Continued)

(58) Field of Classification Search
None
See application file for complete search history.

(56) References Cited

U.S. PATENT DOCUMENTS

| 7,162,061 B1* | 1/2007 | Takeo | G06T 7/0012 |
| | | | 382/128 |
| 2014/0214391 A1* | 7/2014 | Cope | G16B 35/20 |
| | | | 703/11 |

(Continued)

FOREIGN PATENT DOCUMENTS

| JP | 2015-533084 A | 11/2015 |
| JP | 2016-504924 A | 2/2016 |

(Continued)

OTHER PUBLICATIONS

Handelman, G. S., et al. "eDoctor: machine learning and the future of medicine." Journal of internal medicine 284.6 (2018): 603-619. (Year: 2018).*

*Primary Examiner* — Avinash Yentrapati
(74) *Attorney, Agent, or Firm* — Oblon, McClelland, Maier & Neustadt, L.L.P.

(57) ABSTRACT

According to one embodiment, a medical examination assistance apparatus includes processing circuitry. The processing circuitry outputs presence/absence of pre-detection for an adverse event at respective time points when a pre-detection model for an adverse event is applied to time-series medical examination data multiple times. The processing circuitry classifies a detection event of the pre-detection model, into a plurality of patterns each defined by a combination of presence/absence of the pre-detection of an adverse event and presence/absence of a medical event related to the adverse event. The processing circuitry calculates a performance indicator for evaluating the pre-detection model based on the number of instances of each pattern.

16 Claims, 13 Drawing Sheets

(51) Int. Cl.
　　　*G16H 50/30*　　　(2018.01)
　　　*G16H 30/20*　　　(2018.01)
　　　*G16H 40/67*　　　(2018.01)
　　　*G16H 40/40*　　　(2018.01)
　　　*G16H 40/63*　　　(2018.01)
　　　*G16H 30/40*　　　(2018.01)

(52) U.S. Cl.
　　　CPC ............ *G16H 40/63* (2018.01); *G16H 40/67* (2018.01); *G16H 50/30* (2018.01)

(56) References Cited

U.S. PATENT DOCUMENTS

| | | | |
|---|---|---|---|
| 2015/0240315 A1* | 8/2015 | Blakemore | A61P 35/00 |
| | | | 703/2 |
| 2016/0237163 A1* | 8/2016 | Sariel | A61P 35/00 |
| 2019/0086911 A1* | 3/2019 | Xin | G05B 13/0275 |
| 2020/0202527 A1* | 6/2020 | Choi | G06V 10/82 |
| 2020/0205740 A1* | 7/2020 | Laszlo | A61B 5/316 |
| 2022/0084662 A1* | 3/2022 | Das | A61B 5/02055 |
| 2022/0165418 A1* | 5/2022 | Li | G06V 10/7747 |
| 2022/0230300 A1* | 7/2022 | Kawczynski | G06T 7/0004 |

FOREIGN PATENT DOCUMENTS

| | | |
|---|---|---|
| JP | 2017-502983 A | 1/2017 |
| JP | 2018-156415 A | 10/2018 |

* cited by examiner

|    | Pre-detection | Implementation of intervention | Adverse event | Number of instances |
|----|---------------|-------------------------------|---------------|---------------------|
| P1 | No            | No                            | No            | 210                 |
| P2 |               |                               | Yes           | 15                  |
| P3 |               | Yes                           | No            | 60                  |
| P4 |               |                               | Yes           | 8                   |
| P5 | Yes           | No                            | No            | 15                  |
| P6 |               |                               | Yes           | 12                  |
| P7 |               | Yes                           | No            | 40                  |
| P8 |               |                               | Yes           | 5                   |

Total: 365

F I G. 9

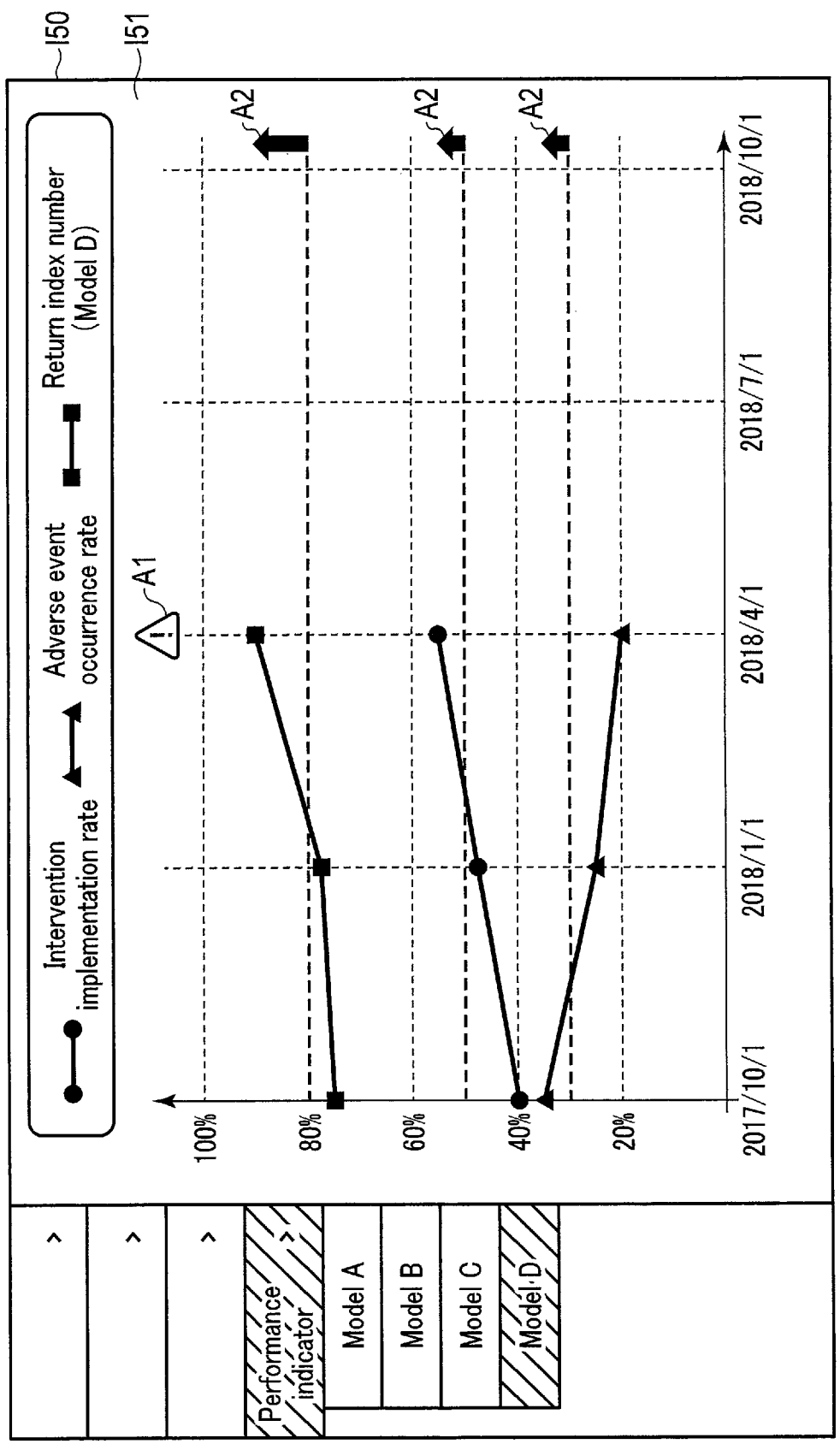
F I G. 14

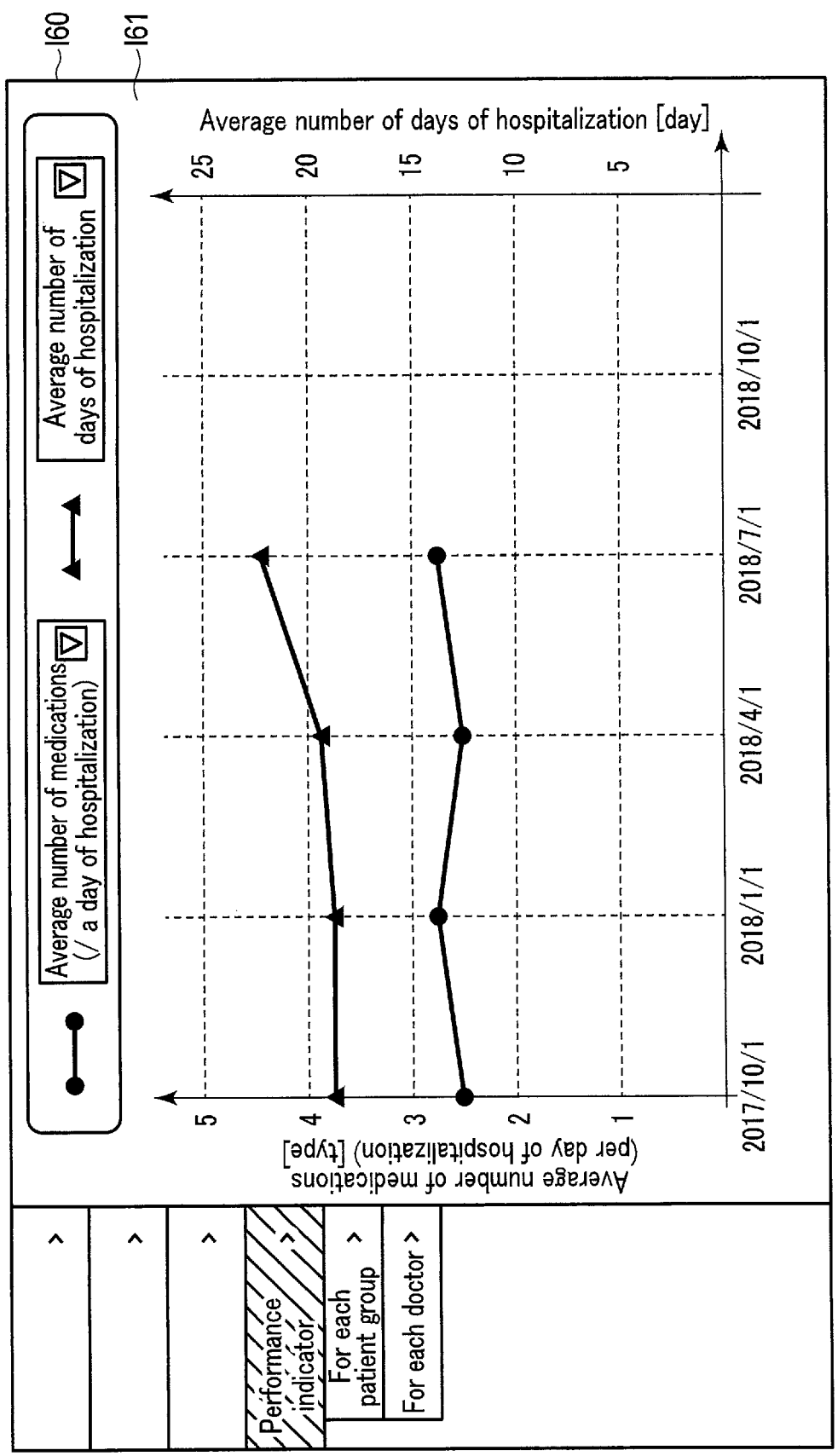
F I G. 15

| Level | Examples of highly invasive intervention event for heart failure |
|---|---|
| 3 | Unscheduled emergency surgery |
| 2 | ECMO |
| 1 | Cardiotonic drug / catecholamine |
| 1 | Diuretic medicine (intravenous injection) |
|  | ... |

F I G. 16A

| Level | Examples of less-invasive intervention event for heart failure |
|---|---|
| 2 | ACE inhibitor |
| 2 | ARB |
| 2 | $\beta$-blocking agent |
| 2 | Diuretic medicine (oral) |
| 1 | Additional imaging test |
| 1 | Additional blood test |
|  | ... |

F I G. 16B

MEDICAL EXAMINATION ASSISTANCE APPARATUS

CROSS-REFERENCE TO RELATED APPLICATIONS

This application is based upon and claims the benefit of priority from the Japanese Patent Application No. 2019-159598, filed Sep. 2, 2019 the entire contents of which are incorporated herein by reference.

FIELD

Embodiments described herein relate generally to a medical examination assistance apparatus.

BACKGROUND

Undesirable medical incidents that occur in patients are collectively called adverse events. The adverse events include, for example, aggravation of a patient's condition due to a disorder, such as heart failure, apoplexy, or the like that requires hospitalization, and occurrence of a side effect of treatment, such as drug-induced hepatic and renal dysfunction. Under such circumstances, there is known a technology of constructing a pre-detection model using actual medical examination data and detecting an adverse event in advance. When an adverse event is detected in advance, an intervention (therapeutic intervention) for preventing the adverse event is performed by a doctor and the like.

However, the adverse event may not be prevented or an unnecessary intervention may be performed depending on the accuracy of the pre-detection. For example, a case where there is pre-detection of an adverse event and a case where there is no pre-detection of an adverse event cannot be observed simultaneously for the same patient. Likewise, a case where there is an occurrence of an adverse event and a case where there is no occurrence of an adverse event cannot be observed simultaneously for the same patient. Therefore, for a case where no adverse event has occurred, it is impossible to distinguish between a case where no adverse event has occurred because an intervention in accordance with the pre-detection was performed and a case where the pre-detection was improper and there was no adverse event irrespective of whether an intervention was performed or not. Namely, it is impossible to verify, for each patient, whether pre-detection performed by a pre-detection model was proper or not. In other words, it is impossible to evaluate the performance of a pre-detection model for preventing an adverse event.

BRIEF DESCRIPTION OF THE DRAWINGS

FIG. 9 is a diagram for explaining an example of a classification result obtained in the classification process for a series of events shown in FIG. 7.

FIG. 14 is a schematic diagram showing an example of a display screen image displayed on the display of the medical terminal shown in FIG. 2 in the display processing of a performance indicator according to a fourth modification.

FIG. 15 is a schematic diagram showing an example of a display screen image displayed on the display of the medical terminal shown in FIG. 2 in the display processing of a performance indicator according to a fifth modification.

FIG. 16A is a diagram for explaining a classification process for a series of events according to a sixth modification.

FIG. 16B is a diagram for explaining the classification process for a series of events according to the sixth modification.

DETAILED DESCRIPTION

In general, a medical examination assistance apparatus according to one embodiment includes processing circuitry. The processing circuitry outputs presence/absence of a pre-detection for an adverse event at respective time points when a pre-detection model of an adverse event is applied to time-series medical examination data multiple times. The processing circuitry classifies a detection event of the pre-detection model with respect to the time points at which the pre-detection model is applied multiple times, into a plurality of patterns each defined by a combination of information on presence/absence of pre-detection for an adverse event and information on presence/absence of a medical event related to the adverse event. The processing circuitry calculates a performance indicator for evaluating the pre-detection model based on the number of instances of each pattern.

Hereinafter, the medical examination assistance apparatus according to the present embodiment will be described with reference to the accompanying drawings. In the descriptions provided below, constituents having the same or almost the same functions will be denoted by the same reference symbols, and a repeat description of such constituents will be given only where necessary. Where the same element is illustrated in different drawings, the dimensions and scales thereof may be different between the drawings.

Figure 1:
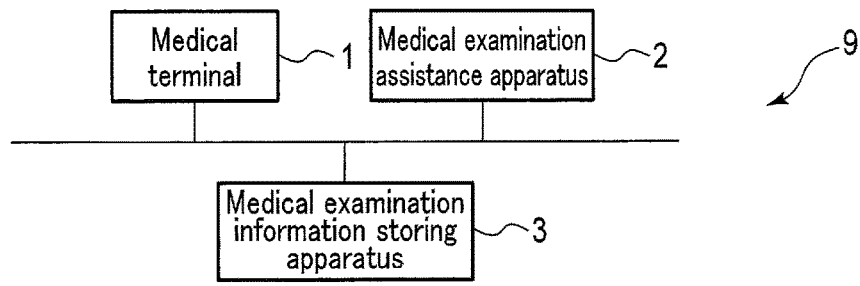
FIG. 1 is a diagram showing a configuration example of a medical examination assistance system including a medical examination assistance apparatus according to an embodiment.
Figure 2:
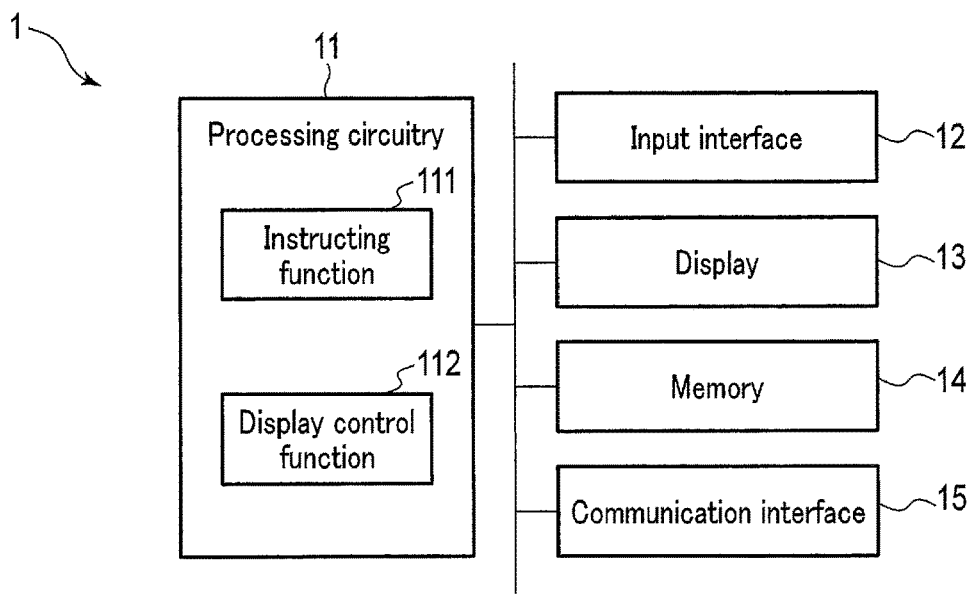
FIG. 2 is a diagram showing a configuration example of a medical terminal shown in FIG. 1.
Figure 3:
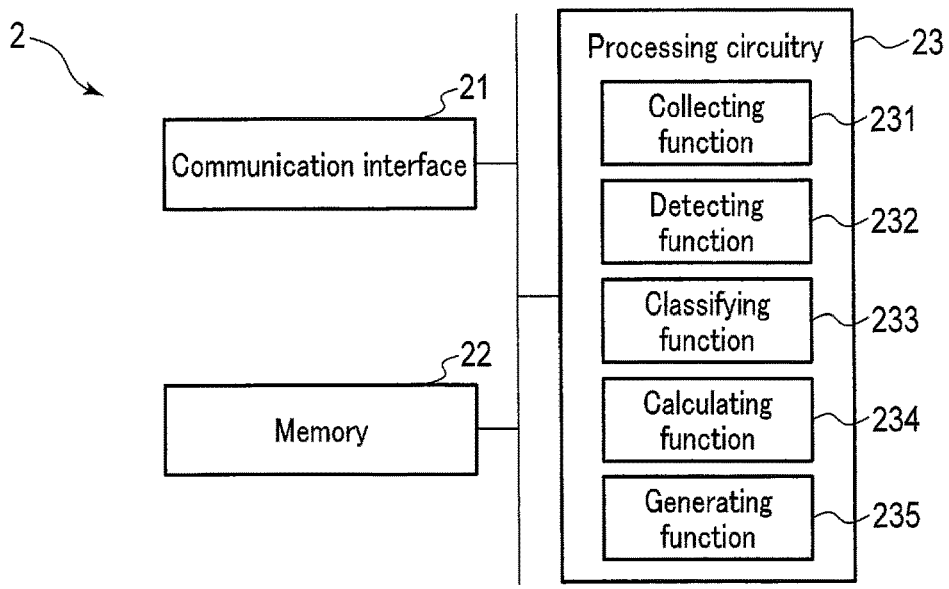
FIG. 3 is a diagram showing a configuration example of a medical examination assistance apparatus shown in FIG. 1.

FIG. 1 is a diagram showing a configuration example of a medical examination assistance system 9 according to the present embodiment. As shown in FIG. 1, the medical examination assistance system 9 includes a medical terminal 1, a medical examination assistance apparatus 2, and a medical examination information storing apparatus 3. FIG. 2 is a diagram showing a configuration example of the medical terminal 1 shown in FIG. 1. FIG. 3 is a diagram showing an example of the medical examination assistance apparatus 2 shown in FIG. 1.

An example will be described below in which the medical terminal 1 and the medical examination assistance apparatus 2 constitute a client server system in which the medical terminal 1 functions as a client and the medical examination assistance apparatus 2 functions as a server, as shown in FIGS. 1 to 3. The medical terminal 1, the medical examination assistance apparatus 2, and the medical examination information storing apparatus 3 are connected to one another via an in-hospital network such as a local area network (LAN) in a communicatory manner, as shown in FIG. 1. The medical terminal 1 and the medical examination assistance apparatus 2 may be integrally configured. In this case, the medical examination assistance system 9 can be represented as a system including the medical examination assistance apparatus 2 further having functions or elements equivalent to those of the medical terminal 1, and the medical examination information storing apparatus 3 (both the medical examination assistance apparatus 2 and the medical examination information storing apparatus 3 described below). Namely, the medical examination assistance system 9 need not include the medical terminal 1.

The medical examination assistance apparatus 2 is an apparatus that receives a processing request from the medical terminal 1 and performs processing corresponding to the received processing request. A predetermined server application corresponding to an integrative viewer installed in the medical terminal 1 is installed in the medical examination assistance apparatus 2. The medical examination assistance apparatus 2 determines, for example, a display form of medical examination data or performance indicator data to be displayed on a display of the medical terminal 1. The performance indicator data is, for example, data showing the result of the performance evaluation regarding the pre-detection model calculated in the medical examination assistance apparatus 2. The medical examination assistance apparatus 2 includes a communication interface 21, a memory 22, and processing circuitry 23, as shown in FIG. 3.

The communication interface 21 performs data communication with external apparatuses, such as the medical terminal 1 and the medical examination information storing apparatus 3. The communication interface 21 includes communication circuitry for performing the data communication. The communication circuitry may be communication circuitry corresponding to wire communication, or communication circuitry corresponding to wireless communication such as Wi-Fi (registered trademark) communication.

The memory 22 is a storage device, such as a hard disk drive (HDD), a solid state drive (SSD), or an integrated circuit storage device, which stores various types of information. The memory 22 may be a drive device which reads and writes various types of information from and to portable storage media such as a compact disc (CD), a digital versatile disc (DVD), a Blu-ray (registered trademark) disc (BD), or a flash memory, other than an HDD, an SSD, or the like. The storage area of the memory 22 may be in the medical examination assistance apparatus 2, or in an external storage apparatus connected via a network. The memory 22 stores, for example, performance indicator data, a medical image file, and medical examination data. The memory 22 temporarily stores various data being processed. The memory 22 also stores the pre-detection model.

The pre-detection model is, for example, a machine learning model. As an algorithm of a machine learning model, a decision tree, a decision forest, a neural network, a support vector machine, clustering, a self-organizing map, a Bayesian network, or the like may be adopted. The pre-detection model is set so as to output the result of the pattern classification, the result of the tallying, or respective performance indicators as medical examination data such as vital sign information is input.

The processing circuitry 23 controls the entire operation of the medical examination assistance apparatus 2. The processing circuitry 23 executes a program related to performance evaluation of the pre-detection model for preventing an adverse event (hereinafter referred to as a "performance evaluation program"), and generates performance indicator data for evaluating the performance of the pre-detection model. The processing circuitry 23 includes, as hardware resources, a processor such as a central processing unit (CPU), a micro processing unit (MPU), or a graphics processing unit (GPU), and a memory such as a read only memory (ROM) and a random access memory (RAM).

With a processor that executes a program loaded into the memory, the processing circuitry 23 according to the present embodiment performs a collecting function 231, a detecting function 232, a classifying function 233, a calculating function 234, and a generating function 235.

The collecting function 231 collects model verification data from, for example, the medical examination information storing apparatus 3. The model verification data includes various data used in a model performance evaluation process. The collected model verification data is stored in a database of the memory 22. In the present embodiment, the model verification data includes medical examination data, which will be described below, and event data.

The detecting function 232 outputs whether or not there is pre-detection of an adverse event at respective time points when a pre-detection model of an adverse event is applied to time-series medical examination data multiple times. Specifically, the detecting function 232 applies the pre-detection model whose performance is to be evaluated to the model verification data, and thereby outputs time-series data showing whether or not there is pre-detection of an adverse event with respect to each model detection time point. The detecting function 232 is an example of a detector.

The classifying function 233 classifies a detection event of the pre-detection model with respect to the time points at which the pre-detection model is applied multiple times, into a plurality of patterns each defined by a combination of information on whether or not there is pre-detection of an adverse event and information on whether or not there was a medical event related to the adverse event. Specifically, the classifying function 233 specifies a series of events corresponding to each model detection time point, and classifies each of the specified series of events into patterns. A series of events relates to a plurality of events occurring in a specific order and period. In addition, the classifying function 233 tallies the number of instances of the series of events classified into each pattern, and outputs the result of the tallying. The classifying function 233 is an example of a classifier.

The calculating function 234 calculates a performance indicator for evaluating the pre-detection model based on the number of instances of each pattern. In other words, the calculating function 234 calculates a performance indicator based on the result of the tallying with regard to the pattern classification. The performance indicator is a value calculated based on the number of instances of each of the following defining the patterns: whether or not there is pre-detection of an adverse event; whether or not an intervention was performed; and whether or not there was an occurrence of an adverse event. The performance indicator includes at least one of an intervention implementation rate, an adverse event occurrence rate, a return index number, a conditional sensitivity, a conditional specificity, a model compliance rate, or a model compliance effective index number. The calculating function 234 is an example of a calculator.

The generating function 235 generates display image data. The display image data includes, for example, image data for displaying the performance indicator. The generated display image data is output to, for example, the medical terminal 1. The generating function 235 is an example of a generator.

The medical terminal 1 is, for example, an apparatus capable of integratively observing medical information. An integrative viewer, which is an application for integratively presenting medical information to a user, is installed in the medical terminal 1. The integrative viewer may be embodied as, for example, a web application, a fat client application, or a thin client application.

As shown in FIG. 2, the medical terminal 1 includes processing circuitry 11, an input interface 12, a display 13, a memory 14, and a communication interface 15. The processing circuitry 11, the input interface 12, the display 13, the memory 14, and the communication interface 15 are connected to one another via, for example, a bus in a communicatory manner.

The processing circuitry 11 controls the entire operation of the medical terminal 1. The processing circuitry 11 includes, as hardware resources, a processor such as a CPU, an MPU, or a GPU, and a memory such as a ROM or a RAM.

With a processor that executes a program loaded into the memory, the processing circuitry 11 according to the present embodiment performs an instructing function 111 and a display control function 112.

The instructing function 111 transmits, for example, a display instruction received via the input interface 12, to the medical examination assistance apparatus 2 via the communication interface 15. The display instruction includes, for example, an instruction for displaying the medical examination data and performance indicator data related to a specific patient.

The display control function 112 displays the display image data received from the medical examination assistance apparatus 2 on the display 13 in a predetermined display form. The predetermined display form may be set in advance and stored in the memory 14 or the like. The display form may be changed according to the output of the input interface 12.

The data received from the medical examination assistance apparatus 2 is not limited to display image data, and may be various values. In this case, the display control function 112, like the processing circuitry 23 of the medical examination assistance apparatus 2 described later, may generate display image data based on the received various values.

The input interface 12 is implemented by, for example, a mouse, a keyboard, and a touch panel to which an instruction is input by touching an operation screen. The input interface 12 receives, for example, a display instruction from an operator. The input interface 12 converts the display instruction from the operator into an electrical signal, and outputs the electrical signal to the processing circuitry 11.

The display 13 displays various types of information. As the display 13, a display of any type can be suitably adopted. For example, a liquid crystal display (LCD), a cathode ray tube (CRT) display, an organic electroluminescence display (OELD), or a plasma display can be adopted as the display 13. Also, the display 13 may be of a desktop type, or configured as a tablet terminal, etc., capable of performing wireless communication with the main body of the medical terminal 1. One or more than one projector may be used as the display 13.

The memory 14 is a storage device, such as an HDD, an SSD, or an integrated circuit storage device, which stores various types of information. The memory 14 may be a drive device which reads and writes various types of information from and to portable storage media such as a CD, a DVD, a BD, or a flash memory, other than an HDD, an SSD, or the like. The storage area of the memory 14 may be in the medical terminal 1, or in an external storage device connected via a network. For example, the memory 14 stores information received from the medical examination assistance apparatus 2.

The communication interface 15 performs data communication with the medical examination assistance apparatus 2 and the medical examination information storing apparatus 3 connected thereto via electrical communication lines such as an in-hospital network. The communication interface 15 includes communication circuitry for performing the data communication. The communication circuitry may be communication circuitry corresponding to wire communication, or communication circuitry corresponding to wireless communication such as Wi-Fi (registered trademark) communication. For the communication with the medical examination assistance apparatus 2 and the medical examination information storing apparatus 3, any standard may be adopted, such as Health Level 7 (HL7) or Digital Imaging and Communications in Medicine (DICOM), or both.

For example, a Vendor Neutral Archive (VNA) system can be used as the medical examination information storing apparatus 3. The VNA system as the medical examination information storing apparatus 3 may be a single system storing various types of information, or a system including a plurality of VNA systems connected to each other. For example, a combination of multiple data servers or the like connected to a network may be used as the medical examination information storing apparatus 3. Hereinafter, the VNA system will be described as an example of the medical examination information storing apparatus 3.

The medical examination information storing apparatus 3 is an integrative archive system that comprehensively manages medical image files stored in medical image management systems (picture archiving and communication systems: PACS) of different manufacturers and various medical examination data managed by respective clinical department systems. The medical examination information storing apparatus 3 is connected to, for example, a PACS (not shown) and an electronic medical record system (not shown) via an in-hospital network, such as a LAN, in a communicatory manner. The various types of information managed by and stored in the medical examination information storing apparatus 3 are not necessarily limited to information obtained from systems of different manufacturers, and may be information obtained from a system of a single manufacturer.

For example, the medical examination information storing apparatus 3 regularly obtains the medical image files stored in the PACS, and stores the medical image files in a memory included in the medical examination information storing apparatus 3. The medical image file is, for example, a file in a format based on the DICOM standard. The medical image file may be reworded as DICOM data. The medical image file is generated by a medical image diagnosis apparatus. The medical image diagnosis apparatus performs an examination by imaging a patient. The medical image diagnosis apparatus includes, for example, an X-ray computed tomography apparatus, an X-ray diagnosis apparatus, a magnetic resonance imaging apparatus, a nuclear medicine diagnosis apparatus, and an ultrasound diagnosis apparatus. The medical image file includes, for example, medical image data and attendant information.

The medical image diagnosis apparatus collects raw data related to a patient by imaging the patient, and generates medical image data based on the collected raw data. The medical image is displayed based on the medical image data.

The attendant information classifies the medical image data and indicates the attribute, type, source, or the like of the medical image data. The attendant information of the medical image file includes information for specifying the medical image, such as a test unique identifier (UID), a series UID, a patient ID, a patient name, a birth date, a modality code, a series description, and the like.

The test UID is an identifier capable of uniquely identifying a test. The series UID is an identifier capable of uniquely identifying a series of images obtained for, for example, each imaging site or imaging condition. The patient ID is provided to each patient, and is an identifier for uniquely identifying the patient in, for example, a single hospital. The patient name represents a name of the patient corresponding to the patient ID. The birth date represents a birth date of the patient corresponding to the patient ID. The modality code is an identifier for identifying a modality type, and defines, for example, "CT", "MR", and "US". The "CT", "MR", and "US" mean that the medical image is captured by an X-ray computed tomography apparatus, a magnetic resonance imaging apparatus, and an ultrasound diagnosis apparatus, respectively. The series description represents the content of a special note when there is any special note that should be left by a laboratory technician for a doctor in the test (imaging).

Also, the medical examination information storing apparatus 3 regularly obtains information on an electronic medical record stored in the electronic medical record system, and stores the information in the memory included in the medical examination information storing apparatus 3. The information on the electronic medical record includes, for example, patient's basic information and medical examination data.

The patient's basic information is information unique to the patient, and includes, for example, a patient ID, a patient name, a birth date, a gender, and an age.

The medical examination data is information on a patient's physical status, medical condition, treatment, and the like obtained by medical staff in the process of medical examination. The medical examination data includes data obtained in various environments, such as data obtained by apparatuses of different manufacturers, data obtained by apparatuses of different versions, or data obtained by the same apparatus with different settings. The medical examination data is not limited to objective data such as a numerical value, and may be non-numeric data such as subjective data represented by letters/characters. The medical examination data includes, for example, test history information, image information, report information, electrocardiographic information, vital sign information, medication history information, medical record description information, and nursing record information.

The test history information is, for example, information representing the history of test results obtained as a result of performing a laboratory test, a bacteria test, and the like on the patient.

The image information is, for example, information representing the location of a medical image obtained, for example, by imaging the patient. The image information includes, for example, information representing the location of a medical image file generated by the medical image diagnosis apparatus as a result of a test.

The report information is, for example, information representing a summary of the conditions and disorders of the patient made by a radiologist in the radiology department interpreting medical images such as an X-ray image, a CT image, an MRI image, and an ultrasonic image in response to a test request from a clinician in the clinical department. The report information includes, for example, interpretation report information representing an interpretation report made by a radiologist with reference to a medical image file stored in the PACS. The report information includes, for example, information representing a patient ID, patient name, and birth date of a patient corresponding to the medical image file to be interpreted.

The electrocardiographic information is, for example, information on an electrocardiographic waveform measured from the patient. The vital sign information is, for example, basic information relating to a patient's life.

The vital sign information includes, for example, a pulse rate, a respiration rate, a body temperature, a blood pressure, and a level of consciousness.

The medication history information is, for example, information representing a history of the amount of medication administered to the patient.

The medical record description information is, for example, information input to the electronic medical records by a clinician or the like. The medical record description information includes, for example, a medical examination record at the time of admission, a patient's medical history, and prescribed medication history.

The nursing record information is, for example, information input to the electronic medical record by a nurse or the like. The nursing record information includes a nursing record, etc., at the time of admission.

The processing circuitry 11, the processing circuitry 23, and the processing circuitry of the medical examination information storing apparatus 3 may be implemented by an application specific integrated circuit (ASIC) or a programmable logic device (PLD). The PLD includes a simple programmable logic device (SPLD), a complex programmable logic device (CPLD), and a field programmable gate array (FPGA).

The functions 111 to 112 and the functions 231 to 235 are not necessarily implemented by a single processing circuit. The processing circuitry may be configured by combining multiple independent processors which respectively execute programs to implement the functions 111 to 112 and the functions 231 to 235.

Next, performance evaluation regarding the pre-detection model for preventing an adverse event (hereinafter referred to as "model performance evaluation") performed in the medical examination assistance system 9 according to the present embodiment will be described with reference to the drawings.

The model performance evaluation according to the present embodiment refers to performance evaluation regarding a "model which pre-detects an acute heart failure within two days before the acute heart failure occurs, based on a feature amount obtained from a vital sign".

The adverse event refers to every undesirable medical incident that occurs to a patient. The adverse event includes aggravation of a patient's condition attributed to a disorder, occurrence of a side effect of treatment, and the like. Examples of the aggravation of a patient's condition attributed to a disorder include heart failure, apoplexy, and the like that require hospitalization. Examples of the occurrence of a side effect of treatment include drug-induced hepatic dysfunction and renal dysfunction.

Generally, in order to predict (pre-detect) and prevent an adverse event, it is necessary to speculate on counterfactuals. However, a case where there is pre-detection of an adverse event and a case where there is no pre-detection of an adverse event cannot be observed simultaneously for the same patient; therefore, it is impossible to determine whether the result of the prediction made by the pre-detection model for each patient (hereinafter referred to as a "model detection result") is proper or not. For example, even when there was detection by the model and no adverse event occurred, it is impossible to identify whether the result of the model detection was inaccurate, or whether the result of the model detection was accurate but no adverse event occurred because an intervention was performed. That is, it is impossible to determine whether or not the model performance has changed, and in particular, whether or not the model performance has degraded at the time of operation.

Figure 4:
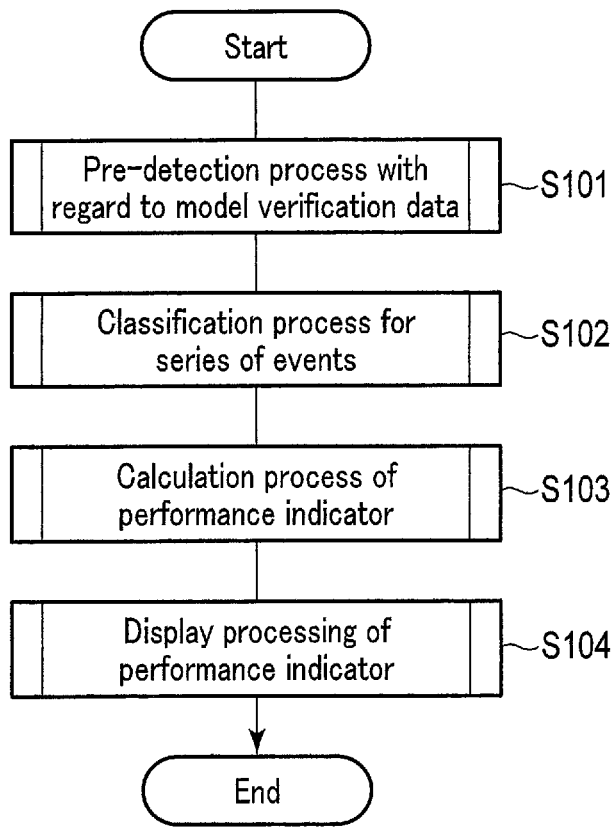
FIG. 4 is a flowchart showing an example of a process related to evaluation of performance of a pre-detection model for preventing an adverse event, performed in the medical examination assistance system shown in FIG. 1.

Accordingly, a performance indicator for evaluating the model performance will be introduced into the model performance evaluation according to the present embodiment, as described below. FIG. 4 is a flowchart showing an example of a process related to evaluation of performance of a pre-detection model for preventing an adverse event (hereinafter referred to as a "model performance evaluation process"), performed in the medical examination assistance system 9 shown in FIG. 1.

In step S101, the detecting function 232 performs a pre-detection process with regard to model verification data (hereinafter referred to as a "detection process"). The detection process will be detailed later. The process then proceeds to step S102.

In step S102, the classifying function 233 performs a classification process for a series of events (hereinafter referred to as a "classification process"). The classification process will be detailed later. The process then proceeds to step S103.

In step S103, the calculating function 234 performs a calculation process of a performance indicator (hereinafter referred to as a "calculation process"). The calculation process will be detailed later. The process then proceeds to step S104.

In step S104, the generating function 235 performs display processing of a performance indicator (hereinafter referred to as "display processing"). The display processing will be detailed later. The model performance evaluation process is then brought to an end.

(Detection Process)

Figure 5:
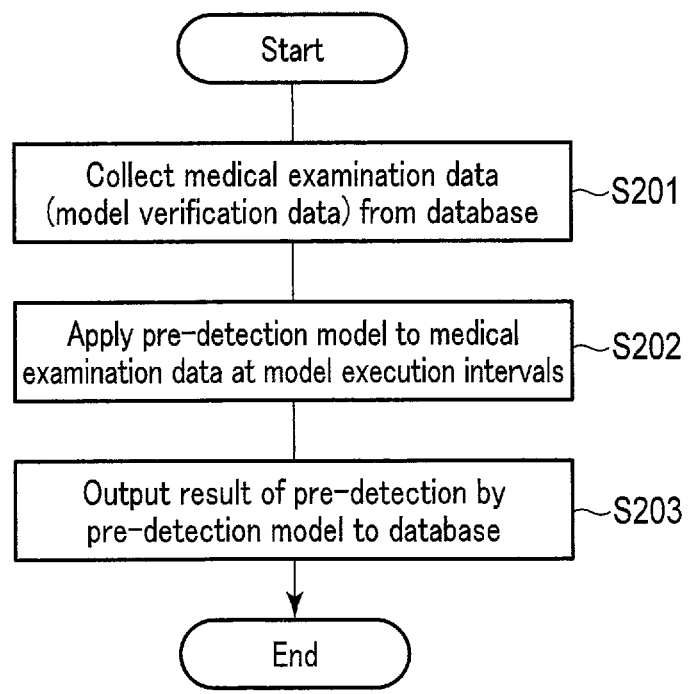
FIG. 5 is a flowchart showing an example of a pre-detection process with regard to model verification data included in the process shown in FIG. 4.
Figure 6:
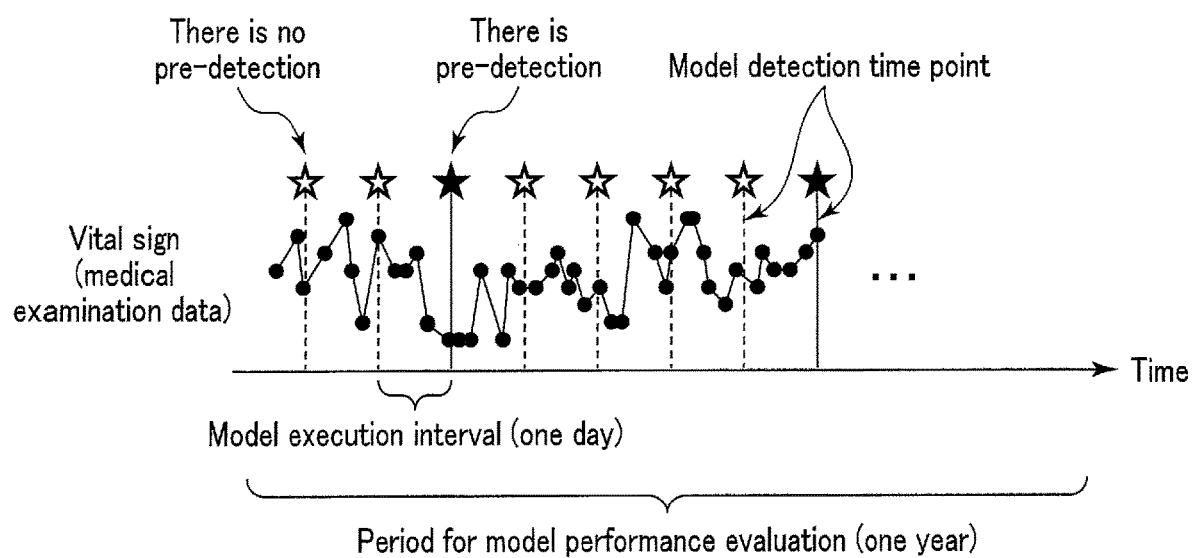
FIG. 6 is a diagram for explaining the pre-detection process with regard to model verification data shown in FIG. 5.

The detection process in step S101 in FIG. 4 will be described in detail with reference to the accompanying drawings. FIG. 5 is a flowchart showing an example of the pre-detection process with regard to model verification data included in the process shown in FIG. 4. FIG. 6 is a diagram for explaining the pre-detection process with regard to model verification data shown in FIG. 5.

In step S201, the collecting function 231 collects time-series medical examination data ranging over a predetermined period for model performance evaluation (i.e., model verification data) from the database of the memory 22. For example, vital sign information is used for the medical examination data. The example shown in FIG. 6 represents a vital sign ranging over the period for model performance evaluation as the collected medical examination data. The predetermined period for model performance evaluation is set to, for example, one year.

In step S202, the detecting function 232 applies a pre-detection model whose performance is to be evaluated to the vital sign information (medical examination data) at predetermined model execution intervals. The predetermined model execution interval is, for example, one day. Accordingly, the pre-detection model is executed at a daily timing (model detection time point), as shown in FIG. 6, and, as a result, information on whether there is pre-detection of an adverse event (there is detection by the model) or there is no pre-detection of an adverse event (there is no detection by the model) is obtained. When the period for performance evaluation of the pre-detection model is one year, for example, as shown in FIG. 6, the pre-detection model is applied with respect to 365 time points.

In step S203, the detecting function 232 outputs, to the memory 22, the result of the model detection obtained by applying the pre-detection model of step S202 to the medical examination data (vital sign information). The result of the model detection is time-series data related to whether or not there is pre-detection of an adverse event, and shows whether or not there is pre-detection of an adverse event at each of the multiple model detection time points. The detection process is then brought to an end.

(Classification Process)

Figure 7:
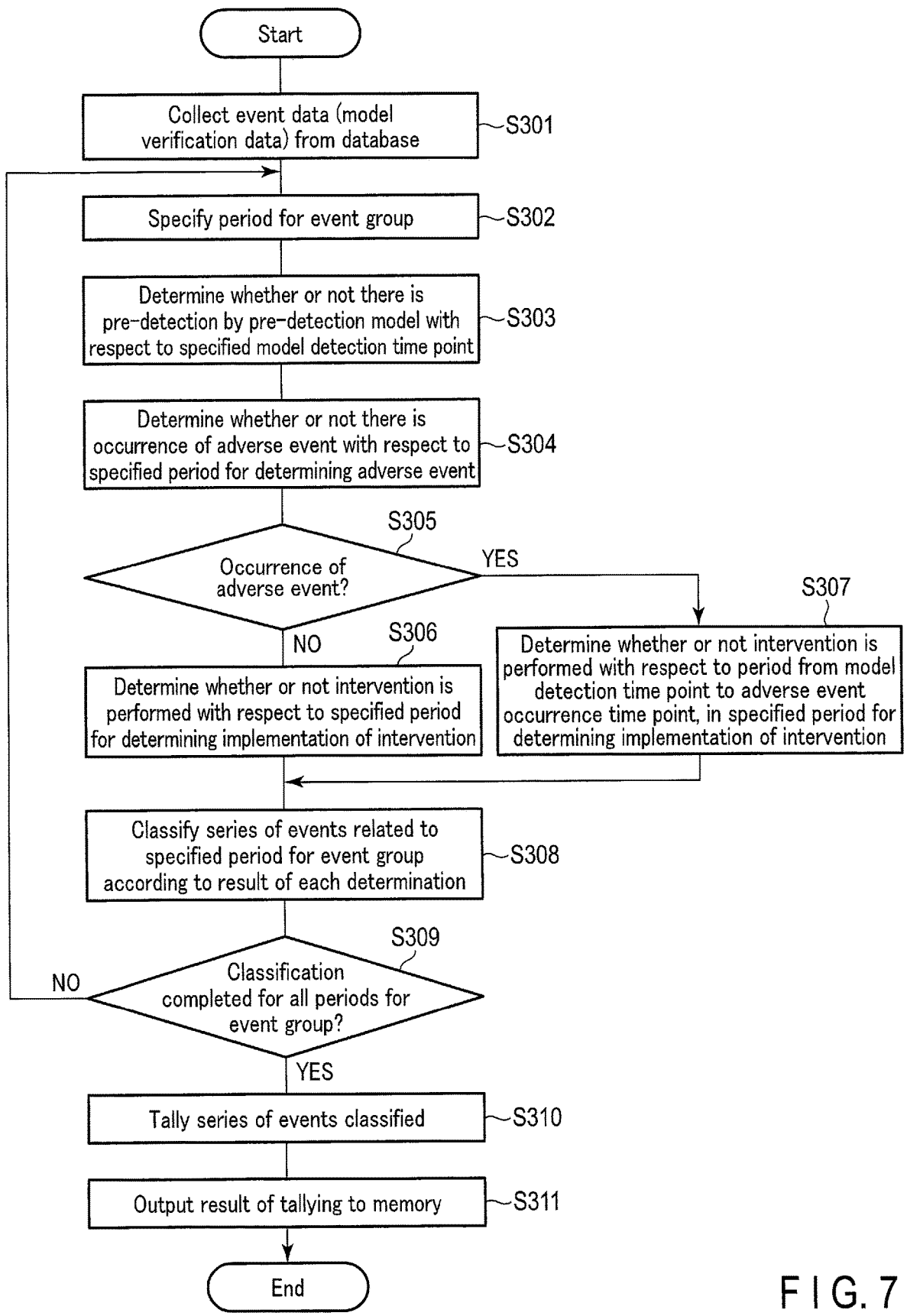
FIG. 7 is a flowchart showing an example of a classification process for a series of events, included in the process shown in FIG. 4.
Figure 8:
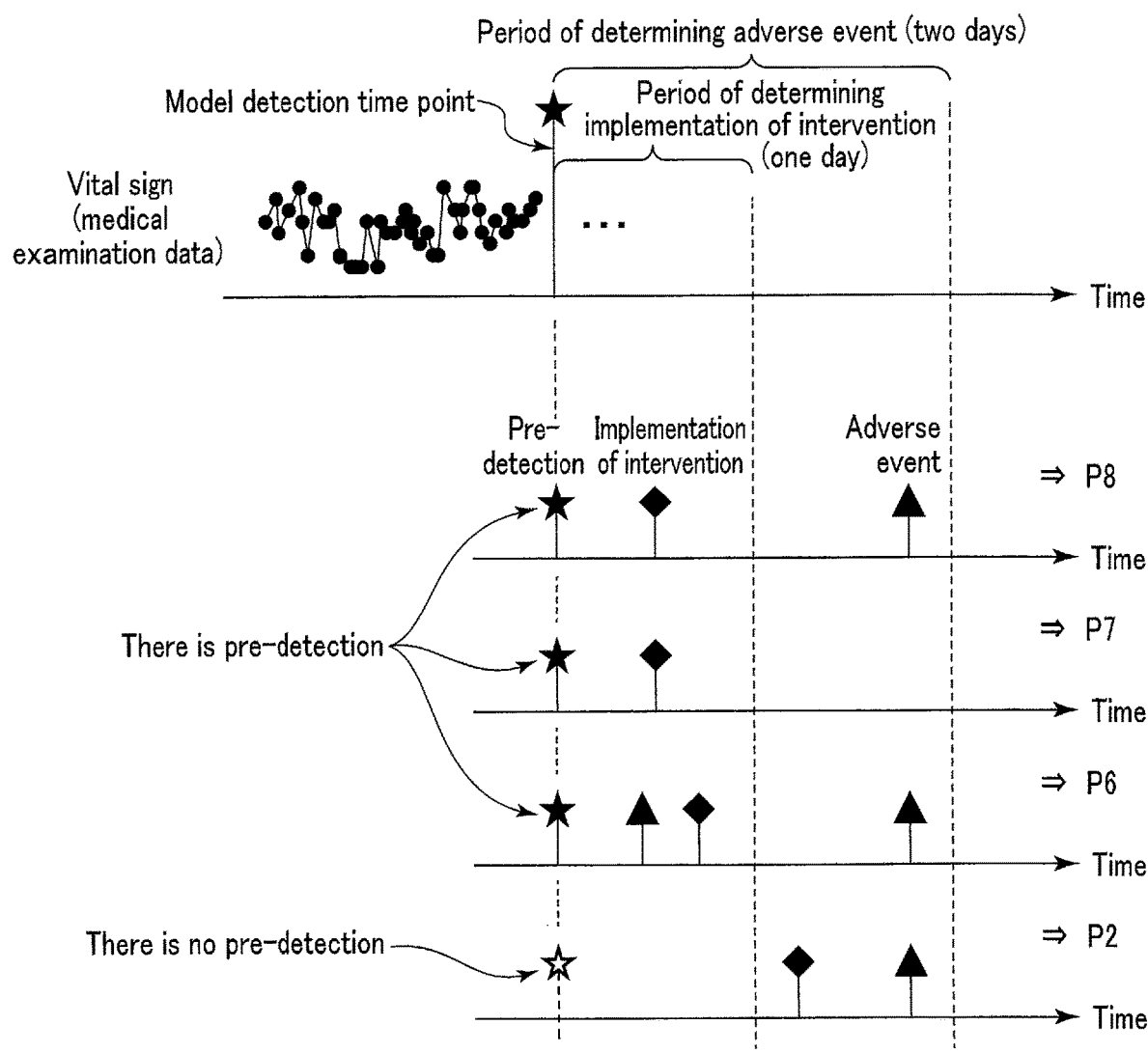
FIG. 8 is a diagram for explaining the classification process for a series of events shown in FIG. 7.

The classification process performed in step S102 in FIG. 4 will be described in detail with reference to the accompanying drawings. FIG. 7 is a flowchart showing an example of the classification process for a series of events included in the process shown in FIG. 4. FIG. 8 is a diagram for explaining the classification process for a series of events shown in FIG. 7. FIG. 9 is a diagram for explaining an example of a result of the classification performed in the classification process for a series of events shown in FIG. 7.

In step S301, the collecting function 231 collects event data (model verification data) from the database of the memory 22. The event data refers to time-series data related to a series of events occurring in a specific order and period such as whether or not there is pre-detection of an adverse event (detection event), whether or not an intervention is performed (intervention event), whether or not there was an occurrence of an adverse event (medical event), and the like. The series of events is a group of events corresponding to any model detection time point, among the groups of events included in the event data.

In step S302, the classifying function 233 specifies the model detection time point (model execution timing). Then, the classifying function 233 specifies a period for the event group. The period for the event group is a period treated as a history of implementation of an intervention and an adverse event corresponding to any model detection result, in the total period of the event data. Namely, whether or not there was an occurrence of the respective events, which are pre-detection, implementation of an intervention, and an adverse event, means whether or not there was an occurrence of the respective events in the period for the event group. The period for the event group begins, for example, at the model detection time point. The period for the event group includes, for example, a period for determining an adverse event and a period for determining implementation of an intervention.

The period for determining an adverse event is a period for determining whether or not an adverse event corresponding to a specified model detection result has occurred. The period for determining implementation of an intervention is a period for determining whether or not implementation of an intervention corresponding to a specified model detection result has occurred. For example, the period for determining an adverse event and the period for determining implementation of an intervention are two days and one day, respectively, as shown on the first line in FIG. 8. In this manner, the period for determining an adverse event (a predetermined period related to whether or not there was an occurrence of an adverse event) and the period for determining implementation of an intervention (a predetermined period related to whether or not an intervention was performed) are independently set.

The period for the event group may be a period beginning at a predetermined time and date, such as 12 o'clock in the morning each day. In this case, a period for determining pre-detection may be provided as a period for determining whether or not there is pre-detection of an adverse event (detection event). Since the pre-detection model is executed at daily intervals in the detection process, the period for determining pre-detection is, for example, one day.

In step S303, the classifying function 233 determines whether or not there is pre-detection by the pre-detection model with respect to a specified model detection time point. The result of the determination is stored, for example, in the memory 22.

In step S304, the classifying function 233 determines whether or not there was an occurrence of an adverse event with respect to a specified period for determining an adverse event. Heart failure does not always occur after an occurrence of a certain event, and it may be difficult to consistently determine heart failure. Therefore, in regard to the determination made in step S304, when an active treatment is needed, that is, when a highly-invasive intervention for heart failure has been performed (the intervention event has occurred), it is determined that an adverse event has occurred. Examples of the implementation of a highly invasive intervention for heart failure include unscheduled emergency surgery, extracorporeal membrane oxygenation (ECMO: a life-support method performed on patients with serious respiratory failure or patients with serious heart failure), use of a cardiotonic drug or catecholamine, and use of a diuretic medicine (intravenous injection). As a matter of course, the death of a patient is determined as an occurrence of an adverse event. The result of the determination is stored, for example, in the memory 22.

For example, an explicit result of determination of whether or not there was an occurrence of heart failure by a doctor or the like may be used to determine whether or not there was an occurrence of an adverse event.

In step S305, the classifying function 233 determines whether or not it was determined that there was an occurrence of an adverse event in step S304. When it is determined that there was an occurrence of an adverse event, the process proceeds to step S307, and when it is not determined as such, the process proceeds to step S306.

In step S306, the classifying function 233 determines whether or not an intervention was performed with respect to a specified period for determining implementation of an intervention. In step S307, the classifying function determines whether or not an intervention was performed with respect to a period from the model detection time point to the time point at which an adverse event occurs, in the specified period for determining implementation of an intervention. In the determinations made in steps S306 and S307 regarding whether or not an intervention was performed, it is determined that an intervention has been performed, for example, when a less-invasive intervention for heart failure has been performed (the intervention event has occurred). Examples of the less-invasive intervention event for heart failure include use of an ACE inhibitor, use of ARB, use of a β-blocking agent, use of a diuretic medicine (oral), and the like. The results of these determinations are stored, for example, in the memory 22.

For example, an explicit result of determination by a doctor or the like on whether or not an intervention was performed may be used to determine whether or not an intervention was performed.

When a medication event is employed as an intervention event, a threshold for a medication period and a dosage amount may be set in order to determine whether or not an intervention is performed.

In step S308, the classifying function 233 classifies a series of events related to a specified period for the event group into a plurality of patterns according to the result of each determination. A series of events includes a result of model detection corresponding to any model detection time point (whether or not there was detection by the model: detection event), a result of determination regarding implementation of an intervention (whether or not an intervention was performed), and a result of determination regarding an occurrence of an adverse event (whether or not there was an adverse event). The plurality of patterns are defined by a combination of information on whether or not there is pre-detection of an adverse event and information on whether or not there was a medical event related to an adverse event, as shown in FIG. 9. The medical event related to an adverse event includes whether or not an intervention was performed and whether or not there was an occurrence of an adverse event. That is, the classifying function 233 classifies a series of events related to each period for the event group, into patterns P1 to P8 according to the presence or absence of each event, as shown in FIG. 9. Said classification will be described in more detail with reference to FIG. 8.

An example of the series of events shown on the second line in FIG. 8 will be considered. In this example, an adverse event is pre-detected at a specified pre-detection time point. An intervention is performed in the period of determining implementation of an intervention. An adverse event occurs in the period of determining an adverse event. Accordingly, this series of events is classified into pattern P8 shown in FIG. 9.

An example of the series of events shown on the third line in FIG. 8 will be considered. In this example, an adverse event is pre-detected at a specified pre-detection time point. An intervention is performed in the period of determining implementation of an intervention. On the other hand, no adverse event occurs in the period of determining an adverse event. Accordingly, this series of events is classified into pattern P7 shown in FIG. 9.

An example of the series of events shown on the fourth line in FIG. 8 will be considered. In this example, an adverse event is pre-detected at a specified pre-detection time point. An intervention is performed in the period of determining implementation of an intervention. However, an adverse event occurs in the period of determining an adverse event and before an intervention is performed. Accordingly, this series of events is regarded as an adverse event having occurred with no intervention performed, and is classified into pattern P6 shown in FIG. 9.

An example of the series of events shown on the fifth line in FIG. 8 will be considered. In this example, no adverse event is pre-detected at a specified pre-detection time point. An intervention is not performed in the period of determining implementation of an intervention. On the other hand, an adverse event occurs in the period of determining an adverse event. Accordingly, this series of events is classified into pattern P2 shown in FIG. 9.

In step S309, the classifying function 233 determines whether or not the classification has been completed for all the periods for the event group. In the present embodiment, the case where the period for the event group is one year and the pre-detection model is executed at daily intervals is described as an example. Therefore, there are 365 periods for all the periods for the event group. If it is not determined that the classification has been completed for all the periods for the event group, the process returns to step S302, and the processing in steps S302 to S309 are repeated. If it is determined that the classification has been completed for all the periods for the event group, the process proceeds to step S310.

In step S310, the classifying function 233 tallies the number of series of events classified into each of the patterns P1 to P8, as shown in FIG. 9, for example.

In step S311, the classifying function 233 outputs, to the memory 22, the result of tallying the series of events classified into each of the patterns P1 to P8. The classifying process is then brought to an end.

As described above, the pre-detection model whose performance is to be evaluated is applied to the time-series medical examination data (model verification data) multiple times. The application of the pre-detection model to the time-series medical examination data performed multiple times may be application to model verification data regarding a single patient, that is, application at multiple time points in a single time series, or application to model verification data regarding multiple patients, that is, application at at least one time point with respect to each of the multiple time series. That is, the total of the tallied number of series of events classified into each pattern is a product of the number of periods for the event group and the number of patients adopted for the process of evaluating the performance of the pre-detection model.

(Calculation Process)

The calculation process performed in step S103 in FIG. 4 will now be detailed. The calculating function 234 calculates a performance indicator IC based on the number of instances of each of the multiple patterns (result of tallying) obtained in the classification process. The performance indicator IC includes at least one of an intervention implementation rate $IC_1$, an adverse event occurrence rate $IC_2$, a return index number $IC_3$, a conditional sensitivity $IC_4$, a conditional specificity $IC_5$, a model compliance rate $IC_6$, or a model compliance effective index number $IC_7$.

In the description provided below, the number of all events is defined as $N_{ALL}$, and the number of events (the number of instances) of each of the patterns P1 to P8 is defined as $N_1$ to $N_8$.

(Intervention Implementation Rate)

The intervention implementation rate $IC_1$ is a performance indicator expressing a degree to which an intervention has been performed in order to prevent occurrence of an adverse event. The intervention implementation rate $IC_1$ is calculated by, for example, formula (1) shown below. For example, the intervention implementation rate $IC_1$ calculated by formula (1) based on the result of the tallying shown in FIG. 9 is 31.0%.

$$IC_1 = \frac{N_3 + N_4 + N_7 + N_8}{N_{ALL}} \times 100. \tag{1}$$

(Adverse Event Occurrence Rate)

The adverse event occurrence rate $IC_2$ is a performance indicator expressing how many adverse events have occurred. The adverse event occurrence rate $IC_2$ is calculated by, for example, formula (2) shown below. For example, the adverse event occurrence rate $IC_2$ calculated by formula (2) based on the result of the tallying shown in FIG. 9 is 11.0%.

$$IC_2 = \frac{N_2 + N_4 + N_6 + N_8}{N_{ALL}} \times 100. \tag{2}$$

(Return Index Number)

The return index number $IC_3$ is a performance indicator expressing a balance between implementation of an intervention and an occurrence of an adverse event. The return index number $IC_3$ is calculated by, for example, formula (3) shown below. Herein, X denotes the number of adverse events occurring when an intervention is not performed at all. For example, when X=100, the return index number $IC_3$ calculated by formula (3) based on the result of the tallying shown in FIG. 9 is 53.1%.

$$IC_3 = \frac{X - (N_2 + N_4 + N_6 + N_8)}{N_3 + N_4 + N_7 + N_8} \times 100. \tag{3}$$

(Conditional Sensitivity)

The conditional sensitivity $IC_4$ is a performance indicator expressing sensitivity of the model estimated by focusing only on a case where no intervention is performed. The conditional sensitivity $IC_4$ is calculated by, for example, formula (4) shown below. For example, the conditional sensitivity $IC_4$ calculated by formula (4) based on the result of the tallying shown in FIG. 9 is 44.4%.

$$IC_4 = \frac{N_6}{N_2 + N_6} \times 100. \tag{4}$$

(Conditional Specificity)

The conditional specificity $IC_5$ is a performance indicator expressing specificity of the model estimated by focusing only on a case where no intervention is performed. The conditional specificity $IC_5$ is calculated by, for example, formula (5) shown below. For example, the conditional specificity $IC_5$ calculated by formula (5) based on the result of the tallying shown in FIG. 9 is 93.3%.

$$IC_5 = \frac{N_1}{N_1 + N_5} \times 100. \qquad (5)$$

(Model Compliance Rate)

The model compliance rate $IC_6$ is a performance indicator expressing a degree to which the model detection result was followed when the determination on the intervention was made. The model compliance rate $IC_6$ is calculated by, for example, formula (6) shown below. For example, the model compliance rate $IC_6$ calculated by formula (6) based on the result of the tallying shown in FIG. 9 is 74.0%.

$$IC_6 = \frac{N_1 + N_2 + N_7 + N_8}{N_{ALL}} \times 100. \qquad (6)$$

(Model Compliance Effective Index Number)

The model compliance effective index number $IC_7$ is a performance indicator expressing the difference in the result between the case where the model is followed and the case where the model is not followed. The model compliance effective index number $IC_7$ is calculated by, for example, formula (7) shown below. For example, the model compliance effective index number $IC_7$ calculated by formula (7) based on the result of the tallying shown in FIG. 9 is 1.04.

$$IC_7 = \log\frac{N_4 + N_6}{N_3 + N_4 + N_5 + N_6} - \log\frac{N_2 + N_8}{N_1 + N_2 + N_7 + N_8}. \qquad (7)$$

(Display Process)

Figure 10:
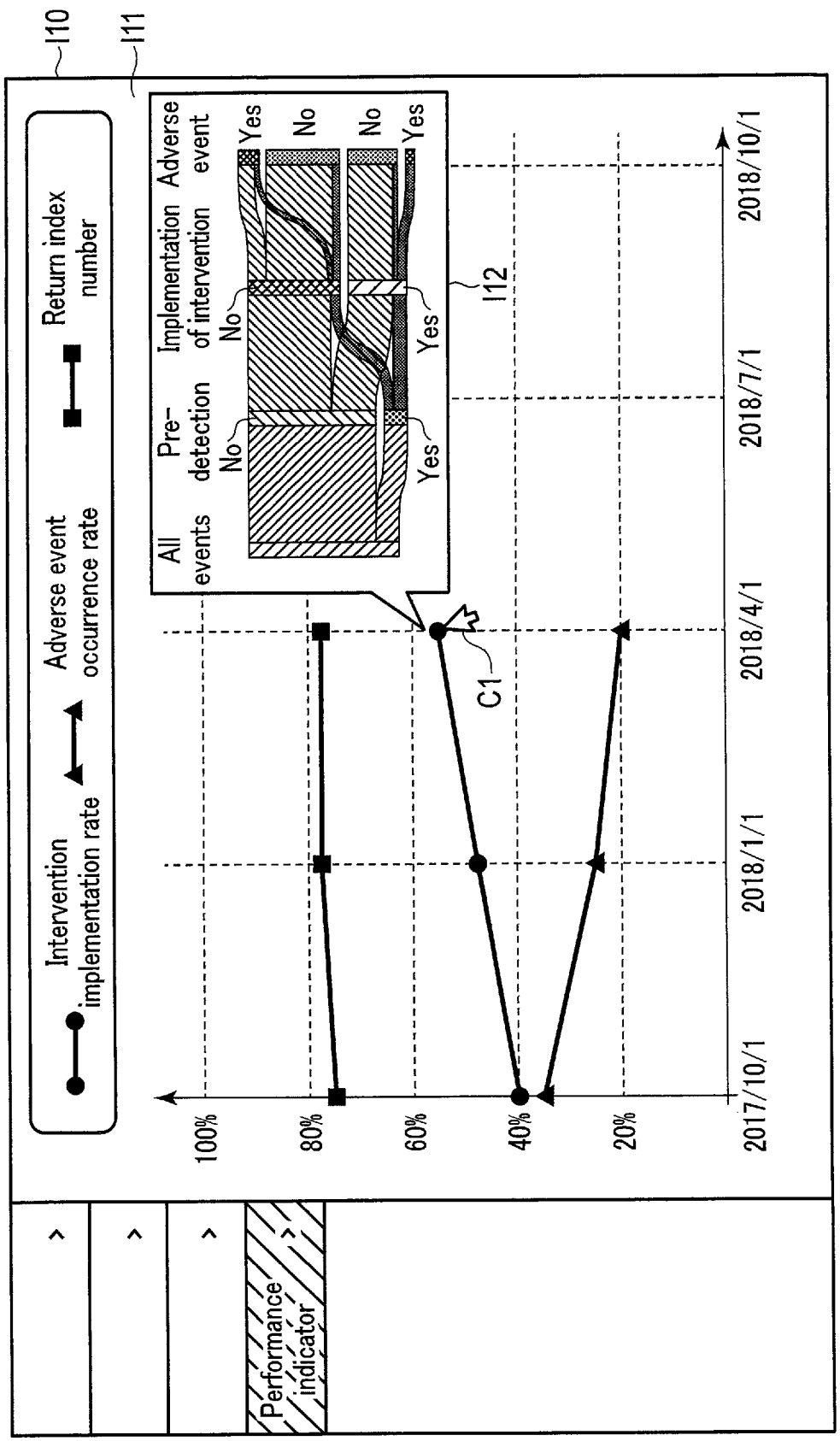
FIG. 10 is a schematic diagram showing an example of a display screen image displayed on a display of the medical terminal shown in FIG. 2 in the display processing of a performance indicator shown in FIG. 4.

The display processing performed in step S104 in FIG. 4 will be described in detail with reference to the accompanying drawings. FIG. 10 is a schematic diagram showing an example of a display screen image I10 displayed on the display 13 of the medical terminal 1 shown in FIG. 2 in the process of displaying a performance indicator shown in FIG. 4.

The generating function 235 generates display image data in order to display the display screen image I10, including the calculated performance indicator. The generated display image data is output to the memory 22 or output to the memory 14 and/or the display 13 of the medical terminal 1. In the medical terminal 1, the display control function 112 causes the display 13 to display the display screen image I10 based on the received display image data. A user can evaluate the model performance based on the displayed performance indicator.

The example in FIG. 10 shows a state in which an item of the "performance indicator" in the display screen image I10 is selected. The selected item is developed to display more detailed information (display I11 of the performance indicator). The display example in FIG. 10 represents the display I11 of the performance indicator using a graph. In the graph, the vertical axis represents a value of each performance indicator, and the horizontal axis represents time.

The display example in FIG. 10 shows the intervention implementation rate $IC_1$, the adverse event occurrence rate $IC_2$, and the return index number $IC_3$ as examples of the performance indicator values. Dates at three-month intervals are shown as examples of the time. The date of each plot shows the timing at which the model performance evaluation process was performed. For example, each plot on Apr. 1, 2018 indicates each performance indicator value calculated with respect to the detection time point from Jan. 1, 2018 to Apr. 1, 2018. In this manner, a value of the performance indicator for each of the multiple detection time points is plotted with respect to multiple detection time points in the display I11 of the performance indicator using the graph. The display screen image I10 may also show time information such as a time and date on which the performance indicator was calculated.

A user such as a doctor can evaluate the model performance based on the displayed performance indicator. For example, when the adverse event occurrence rate $IC_2$ does not decrease while the intervention implementation rate $IC_1$ increases, it is determined that the model performance has degraded. When the adverse event occurrence rate $IC_2$ increases while the intervention implementation rate $IC_1$ does not change, for example, it is determined that the model performance has degraded. Namely, the user can evaluate the model performance based on a ratio of the adverse event occurrence rate $IC_2$ with respect to the intervention implementation rate $IC_1$.

The return index number $IC_3$ is expressed using a ratio of the adverse event occurrence rate $IC_2$ to the intervention implementation rate $IC_1$, as shown in formulas (1) to (3). Specifically, when the ratio of the adverse event occurrence rate $IC_2$ to the intervention implementation rate $IC_1$ increases, a value of the return index number $IC_3$ becomes small. Namely, the user can also determine that the model performance has degraded based on the decrease in the return index number $IC_3$.

The performance indicator values are not limited to the intervention implementation rate $IC_1$, the adverse event occurrence rate $IC_2$, and the return index number $IC_3$, and other performance indicators described above may be displayed in a similar manner. For example, when administration of a medicament or a treatment method that was not assumed at the time of creating the pre-detection model is performed as a therapeutic intervention, the number of instances classified into the pattern in which there was no detection by the model and an intervention was performed increases. According to the art of the present embodiment, even such a case can be detected as a change in the return index number $IC_3$ or the model compliance rate $IC_6$, that is, degradation of the model performance.

The model performance evaluation process is performed at regular intervals, such as every three months. When it is determined that the model performance has degraded based on the performance indicator, the pre-detection model is updated.

The model performance evaluation process is not necessarily performed at regular intervals. The model performance evaluation process may be performed, for example, when administration of a medicament or a treatment method that was not assumed at the time of creating the pre-detection model is performed as a therapeutic intervention, or when the patient's condition has changed.

A series of steps of the model performance evaluation process may be divided. For example, the processes up to the classification process may be performed periodically to accumulate the results of the tallying processing in the memory 22, etc., and then the display processing may be performed at a timing according to an operation by the user. Likewise, the results of the classification process and the results of the detection may be accumulated, so that another process is performed at a timing according to an operation by the user.

Some of the processes of the model performance evaluation process may be performed outside the medical examination assistance apparatus 2 such as the medical terminal 1. For example, the calculated performance indicator may be transmitted to the medical terminal 1, so that the display image data is generated in the medical terminal 1. Also, for example, the detection results and the like may be transmitted to the medical terminal 1, so that the performance indicator is calculated in the medical terminal 1.

Each performance indicator may be calculated and displayed for each patient. At this time, the determination regarding the performance evaluation of the pre-detection model includes a determination on whether or not the pre-detection model is suitable to the current condition of the patient. Namely, according to the art of the present embodiment, it is also possible to evaluate the performance of a pre-detection model tuned to each patient.

In the display processing performed in step S104 in FIG. 4, the respective performance indicator values may be plotted on the basis of the timing (period) related to the date on which an event was actually observed, or may be plotted on the basis of the model detection time point. For example, the performance indicator values plotted on Apr. 1, 2018 may be calculated based on the number of adverse events that occurred in the period from Jan. 1, 2018 to Apr. 1, 2018. In this case, an adverse event that occurred on or after Apr. 2, 2018 is not used to calculate the performance indicators.

A display scale of the graph used in the display I11 of the performance indicators may be changed in the display processing performed in step S104 in FIG. 4. For example, when the scale on the horizontal axis is changed, the respective performance indicator values may be recalculated according to the display interval at the time of the change.

To give further detailed information, a display 112 of the pattern classification may be performed in the display processing performed in step S104 in FIG. 4. The display 112 of the pattern classification is performed, for example, upon operation by the user. For example, when the cursor Cl is on the plot as shown in FIG. 10, or when the plot is selected, the result of the classification process used to calculate the performance indicator corresponding to the plot is displayed in the form of the display 112 of the pattern classification. These user operations are acquired by the input interface 12 of the medical terminal 1, for example. The display example in FIG. 10 shows a Sankey diagram as the display 112 of the pattern classification. The Sankey diagram shows a distribution of the number of instances of each of the patterns P1 to P8. More specifically, the Sankey diagram shows a transition among the events of whether or not there is pre-detection of an adverse event, whether or not an intervention was performed, and whether or not there was an occurrence of the adverse event in terms of the number of instances thereof. The thickness of the arrow representing the transition is determined according to the number of instances.

With this configuration, the user can further confirm the degree to which the model detection result was followed to perform an intervention. The user can further confirm the determination and the measures performed when an adverse event occurred as well as the cause of the occurrence of the adverse event, such as whether or not the model detection was proper, whether or not an intervention was performed according to the model detection, and whether or not an intervention was performed before the adverse event occurred.

As described above, the medical examination assistance system 9 according to the present embodiment calculates the performance indicators of the pre-detection model for preventing an adverse event based on the series of events ("whether or not there was detection by the model", "whether or not an intervention was performed", and "whether or not there was an occurrence of an adverse event") that occur in a specific order and period. In the calculation of the performance indicators, the series of events are classified into patterns and tallied for each pattern. The performance indicators calculated in this manner are displayed, so that the user can evaluate the model performance.

[Modifications]

Hereinafter, a medical examination assistance apparatus according to each modification will be described with reference to the accompanying drawings. In regard to the modifications, mainly the differences from the above-described embodiment will be described. In the descriptions provided below, constituents having the same or almost the same functions as those included in the above-described embodiment will be denoted by the same reference symbols, and a repeat description of such constituents will be given only where necessary.

(First Modification)

Figure 11:
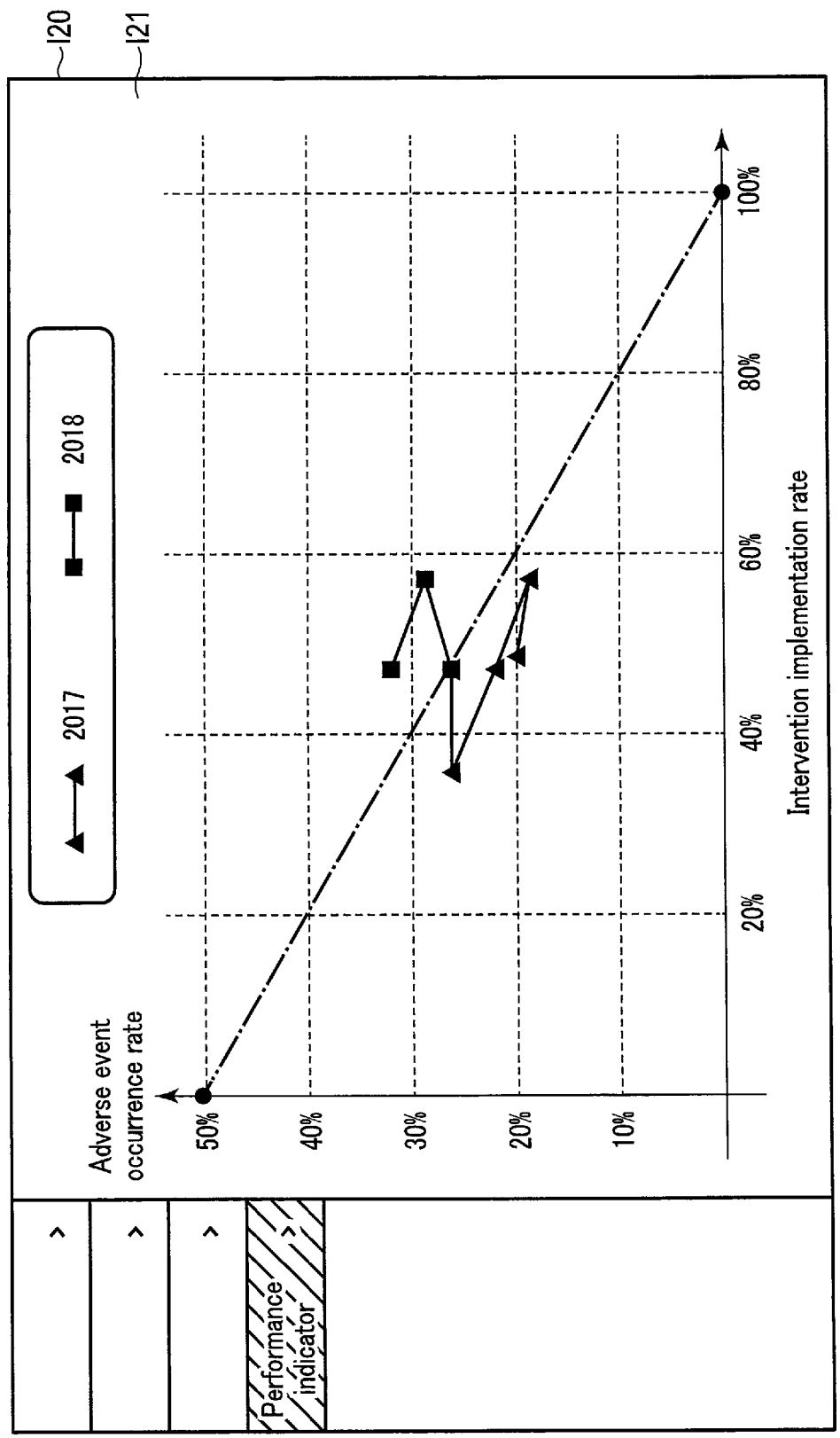
FIG. 11 is a schematic diagram showing an example of a display screen image displayed on the display of the medical terminal shown in FIG. 2 in the display processing of a performance indicator according to a first modification.

A graph used in a display 121 of the performance indicators in the display processing performed in step S104 in FIG. 4 is not limited to the graph of the display example shown in FIG. 10. FIG. 11 is a schematic diagram showing an example of a display screen image 120 displayed on the display 13 of the medical terminal 1 shown in FIG. 2 in the display processing of a performance indicator according to the present modification. In the graph used in the display 121 of the performance indicators of the display screen image 120 according to the present modification, the vertical axis and the horizontal axis represent the adverse event occurrence rate $IC_2$ and the intervention implementation rate $IC_1$, respectively, as shown in FIG. 11. Namely, the dashed-dotted line in the graph of the display example in FIG. 11 represents the return index number $IC_2$. Therefore, according to the art of the present modification, the user can determine that the model performance has degraded when the plot of each performance indicator moves to the upper right or the lower left, that is, when the plot of each performance indicator moves away from the dashed-dotted line.

(Second Modification)

In the display processing performed in step S104 in FIG. 4, when the value of each performance indicator satisfies a predetermined condition, the user may be notified thereof in order to determine whether or not the model performance has degraded.

Figure 12:
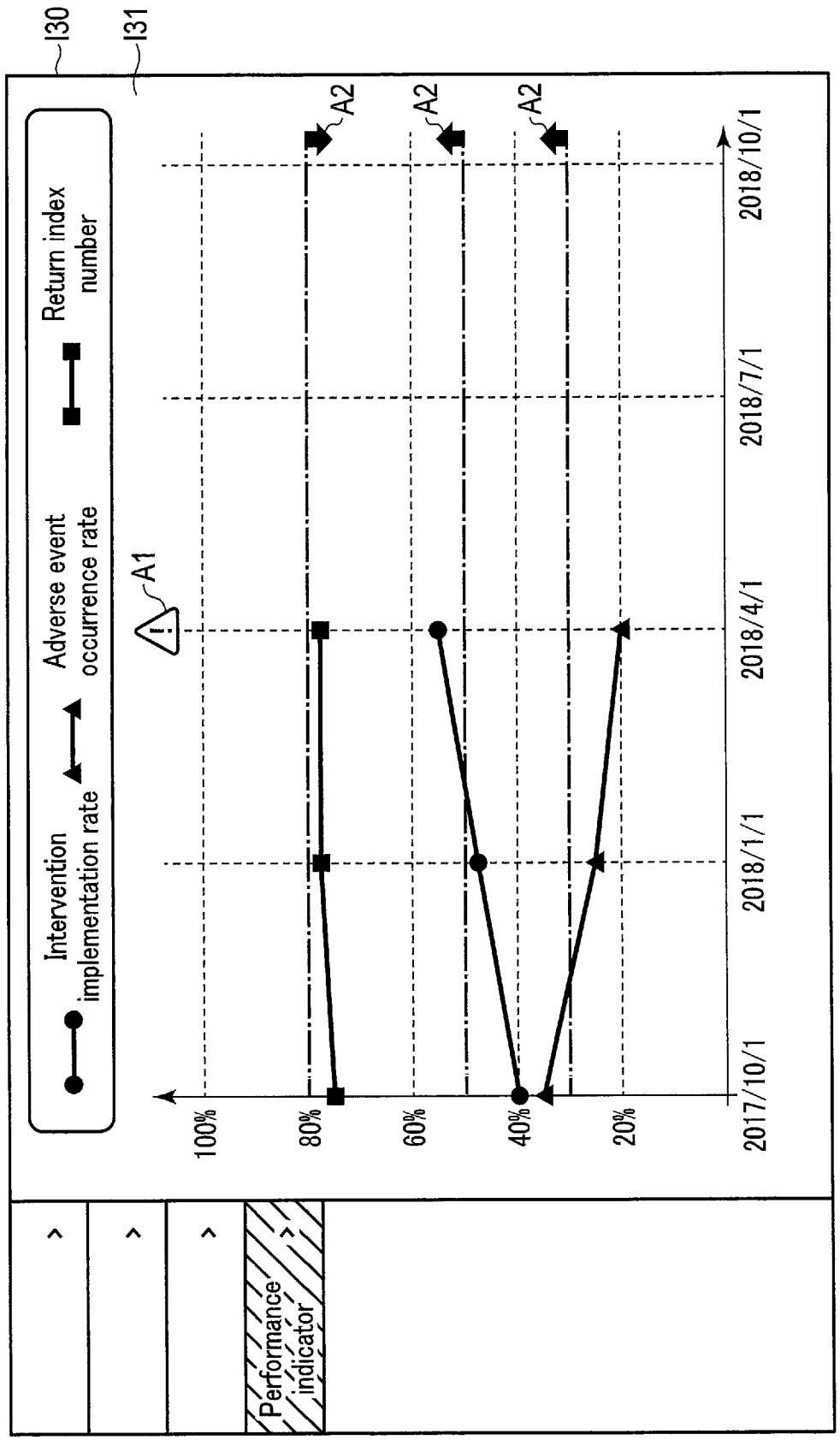
FIG. 12 is a schematic diagram showing an example of a display screen image displayed on the display of the medical terminal shown in FIG. 2 in the display processing of a performance indicator according to a second modification.

FIG. 12 is a schematic diagram showing an example of a display screen image 130 displayed on the display 13 of the medical terminal 1 shown in FIG. 2 in the display processing of a performance indicator according to the present modification. FIG. 12 shows a threshold of each performance indicator and a difference between each performance indicator value and the threshold, using a broken line and an arrow A2.

Various thresholds and/or threshold ranges adopted in the present modification are, for example, set in advance and stored in the memory 22, or the like. For example, the generating function 235 according to the present embodiment determines whether or not each performance indicator value exceeds a predetermined threshold range. Said determination is not necessarily performed for all the performance indicator values, but may be performed for, for example, at least one type of performance indicator value set in advance.

When it is determined that each performance indicator value exceeds the threshold range, the generating function 235 notifies the user thereof. The notification is made using an icon A1 displayed together with the graph of the display 131 of the performance indicators, as shown in FIG. 12, for example. In other words, when it is determined that each performance indicator value exceeds a predetermined threshold range, the generating function 235 generates image data for displaying a notification image which notifies the user that the performance of the pre-detection model has degraded. The notification image includes the icon A1. The icon A1 may be displayed in a blinking manner. The threshold of each performance indicator and the difference between the threshold and each performance indicator value may also be displayed, as indicated by the broken line and the arrow A2.

As described above, according to the art of the present modification, the user can easily recognize the degradation of the model performance. The processing circuitry 23 may be configured to not only evaluate the model performance using each performance indicator value and determine whether or not the model performance has degraded, as described above, but also perform an updating function to update the pre-detection model when it is determined that the model performance has degraded.

(Third Modification)

Figure 13:
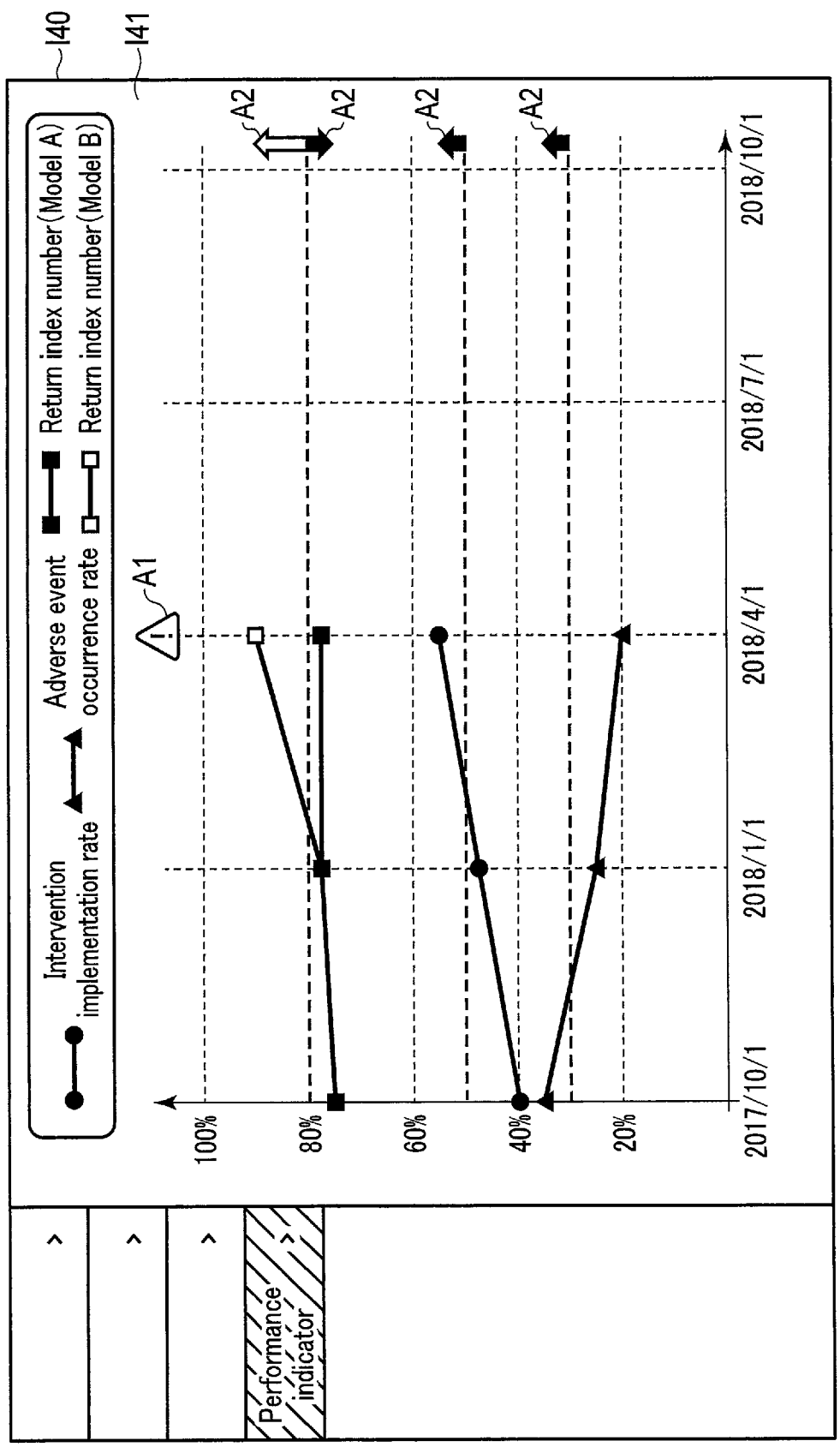
FIG. 13 is a schematic diagram showing an example of a display screen image displayed on the display of the medical terminal shown in FIG. 2 in the display processing of a performance indicator according to a third modification.

In the display processing performed in step S104 in FIG. 4, performance indicators for a plurality of pre-detection models may be displayed. FIG. 13 is a schematic diagram showing an example of a display screen image 140 displayed on the display 13 of the medical terminal 1 shown in FIG. 2 in the display processing of a performance indicator according to the present modification. In the graph used in a display 141 of the performance indicators, the values of the performance indicators are plotted for each pre-detection model, as shown in FIG. 13. In the display example shown in FIG. 13, the return index number $IC_3$ calculated using a model detection result by a model B is further displayed with respect to the model detection time point from Jan. 1, 2018 to Apr. 1, 2018. In this manner, according to the art of the present modification, the user can easily compare the model performance of two or more pre-detection models.

(Fourth Modification)

In the display processing performed in step S104 in FIG. 4, performance indicators for a plurality of pre-detection models may be displayed. FIG. 14 is a schematic diagram showing an example of a display screen image I50 displayed on the display 13 of the medical terminal 1 shown in FIG. 2 in the display processing of a performance indicator according to the present modification. As shown in FIG. 14, the display screen image I50 is provided with a tab for switching the screen image for each of the pre-detection models to be compared. The display example in FIG. 14 shows a state in which a model D is selected. As the number of pre-detection models to be compared and the number of performance indicators to be compared increase, the display screen image may become difficult to see. Therefore, according to the art of the present modification, the user can easily compare the model performance with respect to a plurality of pre-detection models and a plurality of performance indicators without damaging the ease of view of the display screen image.

(Fifth Modification)

In the display processing performed in step S104 in FIG. 4, the performance indicators to be displayed are not limited to those described above, and other performance indicators may also be displayed. FIG. 15 is a schematic diagram showing an example of a display screen image I60 displayed on the display 13 of the medical terminal 1 shown in FIG. 2 in the display processing of a performance indicator according to the present modification.

As other performance indicators, economic outcomes such as cost and a clinical outcomes such as a mortality rate for a group to which the pre-detection model is applied are further calculated. These performance indicators (hereinafter referred to as "outcome indicators") are, for example, calculated by the calculating function 234 based on data collected from the medical examination information storing apparatus 3 or the like. Each of the indicators calculated is output to the memory 22. The generating function 235 generates image data for displaying a display image including the outcome indicators. As the outcome indicator, for example, at least one of a total mortality rate, an in-hospital mortality rate, a readmission rate, a surgery implementation rate, the number of days of hospitalization, medical costs, the number of inspections per day, or the number of medications per day is adopted.

The total mortality rate may be limited to a cause of death associated with a specific disorder. The in-hospital mortality rate may be limited to a cause of death associated with a specific disorder. The readmission rate may be limited to unscheduled readmission. The surgery implementation rate may be limited to unscheduled surgery. The number of days of hospitalization may be limited to hospital wards such as an ICU and a CCU. The medical costs may be limited to a specific medical-cost item. The number of examinations per day may be limited to inpatient or outpatient. The number of medications per day may be limited to inpatient or outpatient. The display example in FIG. 15 shows the average number (type) of medications per day of hospitalization and the average number of days of hospitalization. For example, the user can suspect unnecessary implementation of an intervention when the average number of days of hospitalization does not change while the average number of medications is increasing. Namely, according to the art of the present modification, the user can evaluate the model performance of the pre-detection model from various perspectives.

The outcome indicators may be displayed together with the performance indicators according to the above-described embodiments and the first to fourth embodiments. Each of the outcome indicators may be calculated for each patient group or for each doctor. At these times, the display may be switched using a tab, as shown in FIG. 15, or the indicators may be displayed on the same screen image, as in the art according to the third modification. In addition, when calculating each outcome for each patient group, a patient group set by classifying patients to which the pre-detection model has been applied according to "whether or not there was detection by the model" or "whether nor not there was an intervention" may be employed.

(Sixth Modification)

In the above-described embodiments, the classification process is described as an example, in which whether or not a highly invasive intervention for heart failure (intervention event) was performed and whether or not a less-invasive intervention for heart failure (intervention event) was performed are used to determine whether or not there was an occurrence of an adverse event and whether or not an intervention was performed, respectively. However, the classification process may be performed based not only on whether or not there was an occurrence of an adverse event and whether or not an intervention was performed, but also on the degree (level) of occurrence of an adverse event and implementation of an intervention. FIGS. 16A and 16B are diagrams for explaining the classification process for a series of events according to the sixth modification.

In the classification process according to the present modification, in step S304 shown in FIG. 7, the classifying function 233 determines whether or not there was an occurrence of an adverse event and the level of occurrence of an adverse event with respect to a specified period for determining an adverse event. Likewise, in steps S306 and S307, the classifying function 233 determines whether or not an intervention was performed and the level of implementation of an intervention with respect to each specified period. In other words, in regard to whether or not there was a medical event, a case where there was a medical event includes multiple levels. For example, FIGS. 16A and 16B show three and two levels, respectively, as examples of the multiple levels. The multiple levels may be used for whether or not there was an occurrence of an adverse event, whether or not an intervention was performed, or both. For example, a result of determination by a doctor or the like may be used to determine the level of occurrence of an adverse event and/or the level of implementation of an intervention.

As described above, in the classification process according to the present modification, the result of the tallying described with reference to FIG. 9, for example, is further divided according to the number of levels and thus is more detailed. Namely, according to the art of the present modification, it is possible to calculate the performance indicator according to the presence or absence and/or the level of the series of events.

According to at least one of the embodiments described above, it is possible to evaluate the performance of the pre-detection model for preventing an adverse event.

The term "processor" used in the foregoing description means circuitry such as a CPU, a GPU, an application specific integrated circuit (ASIC), or a programmable logic device (PLD). The PLD includes a simple programmable logic device (SPLD), a complex programmable logic device (CPLD), and a field programmable gate array (FPGA). The processor implements functions by reading and executing the programs stored in the storage circuitry. The storage circuitry storing the programs is a computer-readable non-transitory storage medium. Instead of storing the programs in the storage circuitry, the programs may be directly incorporated into the circuitry of the processor. In this case, the processor implements functions by reading and executing the programs incorporated into the circuitry. The functions corresponding to the programs may be implemented by a combination of logic circuits, rather than by executing the programs. Each processor of the present embodiment is not necessarily configured as a single circuit, but may include a plurality of units of independent circuitry to implement the functions of the processor. Furthermore, the plurality of components shown in FIGS. 1, 2, and 3 may be integrated into a single processor to implement the functions.

The processing circuitry 23 may include a circuitry configuration having similar functions as the machine learning model according to the embodiments that is trained to have parameters so as to output the result of the pattern classification, the result of the tallying, or the respective performance indicators when medical examination data such as vital sign information is input. The circuitry configuration is realized by, for example, an integrated circuit such as ASIC or PLD.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical examination assistance apparatus comprising processing circuitry configured to:
   output whether or not there is pre-detection of an adverse event at respective time points at which a pre-detection model of an adverse event is applied to time-series medical examination data multiple times;
   classify a detection event of the pre-detection model with respect to the time points at which the pre-detection model is applied multiple times, into a plurality of patterns each defined by a combination of whether or not there is pre-detection of an adverse event, and whether or not there is a medical event related to the adverse event;
   calculate a performance indicator for evaluating the pre-detection model based on a count of instances of each of the patterns.

2. The medical examination assistance apparatus according to claim 1, wherein
   said whether or not there is a medical event related to the adverse event includes whether or not an intervention is performed and whether or not there is an occurrence of an adverse event,
   the plurality of patterns are defined by a combination of whether or not there is pre-detection of an adverse event, whether or not an intervention is performed, and whether or not there is an occurrence of an adverse event.

3. The medical examination assistance apparatus according to claim 1, wherein in regard to said whether or not there is a medical event related to the adverse event, a case where there is a medical event related to the adverse event includes multiple levels.

4. The medical examination assistance apparatus according to claim 1, wherein
   said whether or not there is a medical event related to the adverse event includes whether or not an intervention is performed in a first predetermined period and whether or not there is an occurrence of an adverse event in a second predetermined period, and
   the first predetermined period and the second predetermined period are independently set.

5. The medical examination assistance apparatus according to claim 4, wherein when the adverse event occurred within the second predetermined period after the adverse event is pre-detected, the processing circuitry determines whether or not an intervention is performed in a period from the pre-detection of the adverse event to the occurrence of the adverse event within the first predetermined period.

6. The medical examination assistance apparatus according to claim 4, wherein when the adverse event did not occur within the second predetermined period after the adverse event is pre-detected, the processing circuitry determines whether or not an intervention is performed in the first predetermined period after the adverse event is pre-detected.

7. The medical examination assistance apparatus according to claim 4, wherein
a first pattern among the plurality of patterns comprises a series of events which are pre-detection of an adverse event, occurrence of the adverse event, and implementation of an intervention, said events occurring in a mentioned order; and
a second pattern among the plurality of patterns comprises a series of events which are pre-detection of an adverse event, implementation of an intervention, and occurrence of the adverse event, said events occurring in a mentioned order.

8. The medical examination assistance apparatus according to claim 1, wherein the processing circuitry is configured to:
generate an image including the calculated performance indicator; and
display the image on a display.

9. The medical examination assistance apparatus according to claim 8, wherein the image includes a graph showing a value of the performance indicator corresponding to the application of the pre-detection model performed multiple times, the value of the performance indicator being plotted with respect to the time points at which the pre-detection model is applied multiple times.

10. The medical examination assistance apparatus according to claim 9, wherein the image further includes a diagram showing a distribution of the count of instances of each of the patterns.

11. The medical examination assistance apparatus according to claim 8, wherein when the calculated performance indicator exceeds a predetermined threshold range, the processing circuitry further generates an image which notifies a user of degradation of performance of the pre-detection model.

12. The medical examination assistance apparatus according to claim 8, wherein the processing circuitry is configured to:
further calculate outcome indicators including an economic outcome and a clinical outcome; and
further generate a display image including the outcome indicators.

13. The medical examination assistance apparatus according to claim 8, wherein the image includes said graph and information on a time at which the performance indicator is calculated.

14. The medical examination assistance apparatus according to claim 1, wherein the application performed multiple times comprises an application performed at multiple time points with respect to a single time series.

15. The medical examination assistance apparatus according to claim 1, wherein the application performed multiple times comprises an application performed at at least one time point with respect to each of multiple time series.

16. The medical examination assistance apparatus according to claim 1, wherein the performance indicator is a value calculated based on a count of instances with regard to whether or not there is pre-detection of an adverse event, whether or not an intervention is performed, and whether or not there is an occurrence of an adverse event, all of which define the plurality of patterns.

\* \* \* \* \*